United States Patent [19]

Yasis et al.

[11] Patent Number: 5,449,550
[45] Date of Patent: Sep. 12, 1995

[54] MECHANICALLY COMPACTED FABRICS FOR ORTHOPEDIC CASTING TAPES

[75] Inventors: Rafael M. Yasis, White Bear Lake; Scott A. Neamy, Forest Lake; Matthew T. Scholz, Woodbury, all of Minn.

[73] Assignee: Minnesota Mining and Manufacturing Company, St. Paul, Minn.

[21] Appl. No.: 299,570

[22] Filed: Sep. 1, 1994

Related U.S. Application Data

[62] Division of Ser. No. 8,161, Jan. 25, 1993, Pat. No. 5,382,445.

[51] Int. Cl.$^6$ ............................................. B32B 7/00
[52] U.S. Cl. .................................. 428/254; 428/225; 428/253; 428/268; 428/910; 602/8
[58] Field of Search ............... 428/254, 268, 273, 285, 428/253, 910, 225; 602/8

[56] References Cited

U.S. PATENT DOCUMENTS

| | | | |
|---|---|---|---|
| 2,765,513 | 10/1956 | Walton | 26/18.6 |
| 3,077,655 | 2/1963 | Runton | 26/18.5 |
| 3,421,501 | 1/1969 | Beightol | 128/90 |
| 3,630,194 | 12/1971 | Boardman | 128/90 |
| 3,686,725 | 8/1972 | Nisbet et al. | 28/74 R |
| 3,787,272 | 1/1974 | Nisbet et al. | 161/89 |
| 3,793,686 | 2/1974 | Nisbet et al. | 28/75 R |
| 3,908,644 | 9/1975 | Neinart et al. | 128/90 |
| 3,932,526 | 1/1976 | Koshar | 260/607 A |
| 3,972,323 | 8/1976 | Boricheski | 128/91 R |
| 4,041,581 | 8/1977 | Diggle, Jr. | 26/18.6 |
| 4,131,114 | 12/1978 | Kirkpatrick et al. | 128/90 |
| 4,134,397 | 1/1979 | Gianakakos et al. | 128/90 |
| 4,376,438 | 3/1983 | Straube et al. | 128/90 |
| 4,411,262 | 10/1983 | von Bonin et al. | 128/90 |
| 4,433,680 | 2/1984 | Yoon | 128/90 |
| 4,441,262 | 4/1984 | Gazzoni | 34/57 D |
| 4,473,671 | 9/1984 | Green | 523/105 |
| 4,502,479 | 3/1985 | Garwood et al. | 128/90 |
| 4,609,578 | 9/1986 | Reed | 428/76 |
| 4,667,661 | 5/1987 | Scholz et al. | 128/90 |
| 4,668,563 | 5/1987 | Buese et al. | 428/230 |
| 4,705,840 | 11/1987 | Buckanin | 128/90 |
| 4,745,912 | 5/1988 | McMurray | 128/90 |
| 4,800,872 | 1/1989 | Buese et al. | 128/90 |
| 4,841,958 | 6/1989 | Ersfeld et al. | 128/90 |
| 4,940,047 | 7/1990 | Richter et al. | 128/90 |
| 4,947,839 | 8/1990 | Clark et al. | 128/90 |
| 4,984,566 | 1/1991 | Sekine et al. | 128/90 |
| 5,014,403 | 5/1991 | Buese | 28/170 |
| 5,027,804 | 7/1991 | Forsyth et al. | 128/90 |
| 5,088,484 | 2/1992 | Freeman et al. | 602/8 |
| 5,169,698 | 12/1992 | Behjati et al. | 428/68 |
| 5,256,134 | 10/1993 | Ingham | 602/8 |

FOREIGN PATENT DOCUMENTS 364716  1/1932  United Kingdom .

*Primary Examiner*—James J. Bell
*Attorney, Agent, or Firm*—Gary L. Griswold; Walter N. Kirn; F. Andrew Ubel

[57] ABSTRACT

The present invention provides an article, comprising: a fabric sheet which has been mechanically compacted; and a curable item coated onto the fabric sheet. The present invention involves compacting a fabric sheet to impart stretchability and conformability to the fabric while minimizing undesirable recovery forces. Suitable fabrics for mechanical compacting are fabrics which comprise fiberglass fibers which are capable of first being mechanically compacted and then being set or annealed in the distorted, state. The article may be in the form of an orthopedic bandage and may optionally contain a microfiber filler associated with the resin.

19 Claims, No Drawings

MECHANICALLY COMPACTED FABRICS FOR ORTHOPEDIC CASTING TAPES

This is a division of application Ser. No. 08/008/161 filed Jan. 25, 1993 now U.S. Pat. No. 5,382,445.

FIELD OF THE INVENTION

This invention relates to sheet materials coated with a curable polymeric resin. More particularly, this invention relates to a curable resin coated sheet material useful in preparing an orthopedic bandage.

BACKGROUND OF THE INVENTION

Many different orthopedic casting materials have been developed for use in the immobilization of broken or otherwise injured body limbs. Some of the first casting materials developed for this purpose involve the use of plaster of Paris bandages consisting of a mesh fabric (e.g., cotton gauze) with plaster incorporated into the openings and onto the surface of the mesh fabric.

Plaster of Paris casts, however, have a number of attendant disadvantages, including a low strength-to-weight ratio, resulting in a finished east which is very heavy and bulky. Furthermore, plaster of Paris casts typically disintegrate in water, thus making it necessary to avoid bathing, showering, or other activities involving contact with water. In addition, plaster of Paris casts are not air permeable, and thus do not allow for the circulation of air beneath the cast which greatly facilitates the evaporation and removal of moisture trapped between cast and skin. This often leads to skin maceration, irritation, or infection. Such disadvantages, as well as others, stimulated research in the orthopedic casting art for casting materials having improved properties over plaster of Paris.

A significant advancement in the an was achieved when polyisocyanate prepolymers were found to be useful in formulating a resin for orthopedic casting materials, as disclosed, for example, in U.S. Pat. No. 4,502,479 (Garwood et al.) and U.S. Pat. No. 4,411,262 (Von Bonin et al.). U.S. Pat. No. 4,502,479 sets forth an orthopedic casting material comprising a knit fabric which is made from a high modulus fiber (e.g., fiberglass) impregnated with a polyisocyanate prepolymer resin such as polyurethane. Orthopedic casting materials made in accordance with U.S. Pat. No. 4,502,479 provide significant advancement over the plaster of Paris orthopedic casts, including a higher strength-to-weight ratio and greater air permeability. However, such orthopedic casting materials tend not to permit tactile manipulation or palpation of the fine bone structure beneath the cast to the extent possible when applying a plaster of Paris cast. In this regard, knit fiberglass materials are not as compressible as plaster, and tend to mask the fine structure of the bone as the cast is applied, e.g., the cam provider may be limited in "feeling" the bone during reduction of the fracture. Although fiberglass fabrics are somewhat radiolucent they sometimes tend to mask the underlying bone structure to x-ray penetration. Oftentimes a fine mesh or a "shadow" can be seen on the x-ray image. This mesh, corresponding to the knitted fiberglass backing, obstructs the penetration of the x-rays and thereby obscures the free detail of the underlying bone on the x-ray image.

Fiberglass backings have further disadvantages. For example, fiberglass backings are comprised of fibers which have essentially no elongation. Because the fiber elongation is essentially nil, glass fabrics da not stretch unless they are constructed with very loose loops which can deform upon application of tension, thereby providing stretching of the fabric. Knitting with loosely formed chain stitches imparts extensibility by virtue of its system of interlocking knots and loose loops.

Like most knitted fabrics, fiberglass knits tend to curl or fray at a cut edge as the yarns are severed and adjacent loops unravel. Fraying and raveling produce unsightly ends and, in the case of an orthopedic cast, frayed ends may interfere with the formation of a smooth cast, and loose, frayed ends may be sharp and irritating after the resin thereon has cured. Accordingly, frayed edges are considered a distinct disadvantage in orthopedic casting tapes. Stretchy fiberglass fabrics which resist fraying are disclosed in U.S. Pat. No. 4,609,578 (Reed), the disclosure of which is incorporated by reference. Thus, it is well known that fraying of fiberglass knits at cut edges can be reduced by passing the fabric through a heat cycle which sets the yarns giving them new three-dimensional configurations based on their positions in the knit. When a fiberglass fabric which has been heat-set is cut, there is minimal fraying and when a segment of yarn is removed from the heat-set fabric and allowed to relax, it curls into the crimped shape in which it was held in the knit. Accordingly, at the site of a cut, the severed yarns have a tendency to remain in their looped or knotted configuration rather than to spring loose and cause fraying.

In processing extensible fiberglass fabrics according to U.S. Pat. No. 4,609,578 (Reed), a length of fabric is heat-set with essentially no tension. The fabric is often wound onto a cylindrical core so large batches can be processed at one time in a single oven. Care must be taken to avoid applying undue tension to the fabric during wind-up on the knitter which would distort the knots and loops. To prevent applying tension to the fabric during winding, the winding operation is preferably performed with a sag in the fabric as it is wound on the core.

Alternatively, U.S. Pat. No. 5,014,403 (Buese) describes a method of making a stretchable orthopedic fiberglass casting tape by knitting an elastic yarn under tension into the fiberglass fabric in the length direction, releasing the tension from the elastic yarn to compact the fabric and removing the elastic yarn from the fabric. The elastic yarn is removed by a combustion process which may cause localized areas of high temperature which may degrade the fiberglass yarns. The physical properties of glass fibers are adversely affected when subjected to temperatures in excess of about 540° C. Heating fiberglass fabrics to temperatures above about 540° C. should be avoided as subjecting the fiberglass to temperatures of greater than about 540° C. can weaken the fiberglass yarns in the fabric which may result in reduced strength of casts made from such fabrics.

From the foregoing, it will be appreciated that what is needed in the art is an orthopedic casting material which has both the advantages of plaster of Paris, e.g., good moldability and palpability of the free bone structure, and the advantages of non-plaster of Paris materials, e.g., good strength-to-weight ratio and good air permeability. In this regard it would be a significant advancement in the art to provide such a combination of advantages without actually using plaster of Paris, thereby avoiding the inherent disadvantages of plaster of Paris outlined herein. It would be a further advancement in the art to provide such non-plaster of Paris orthopedic casting materials which have as good or better properties than the non-plaster of Paris orthopedic casting materials of the prior art. Such orthopedic casting materials and methods for preparing the same are disclosed and claimed herein.

RELATED APPLICATIONS

Of related interest are the following U.S. patent applications, filed on Jan. 25, 1993 by the assignee of this invention: Microfiber Fillers for Orthopedic Casting Tapes—Ser. No. 08/008,755 now U.S. Pat. No. 5,354,254; Microcreping of Fabrics for Orthopedic Casting Tapes—Ser. No. 08/008,751 now U.S. Pat. No. 5,465,643; Water Curable Resin Compositions—Ser. No. 08/008,743 now U.S. Pt. No. 5,346,439; Orthopedic Support Materials and Method—Ser. No. 08/008,678 now U.S. Pat. No. 5,364,693; and Fabric Backing for Orthopedic Support Materials—Ser. No. 08/009,923 now U.S. Pat. No. 5,411,796 which are herein incorporated by reference.

SUMMARY OF THE INVENTION

The present invention provides an article, comprising: a fiberglass fabric sheet which has been mechanically compacted and heat set; and a curable resin coated onto the fabric sheet. The article may be in the form of an orthopedic bandage and may optionally contain a plurality of microfiber fillers dispersed into the resin. The article may be in the form of a water-hardenable medical dressing capable of immobilizing and/or supporting a body part. This hardenable dressing can be used in tape, sheet, film, slab, or tubular form to prepare orthopedic casts, splints, braces, supports, protective shields, orthotics, and the like. Additionally, other constructions in prefabricated shapes can be used. As used herein the terms "orthopedic support material" or "orthopedic casting material" are used to encompass any of these forms of dressings, and "cast" or "support" are used to include any of these orthopedic support structures.

DETAILED DESCRIPTION OF THE INVENTION

The present invention relates to orthopedic casting materials and methods for preparing and using such orthopedic casting materials, wherein the materials comprise a fiberglass backing or fabric which is impregnated with a curable liquid resin. In particular, the fabrics employed in the present invention have important characteristics and physical properties which allow the fabrics to be made highly extensible.

One element of this invention is a flexible sheet upon which a curable resin can be coated to reinforce the Sheet when the resin is cured thereon. The sheet is preferably porous such that the sheet is at least partially impregnated with the rosin. Examples of suitable sheets are knit fabrics comprised of inorganic fibers or materials such as fiberglass. The sheet may alternatively be referred to as the "scrim" or the "backing."

The present invention involves mechanically compacting a fabric sheet to impart stretchability and conformability to the fabric while minimizing undesirable recovery forces.

Suitable fabrics, after mechanical compacting, have important characteristics and physical properties which allow the fabrics to be resin loaded to the extent needed to provide proper strength as an orthopedic casting material, while providing necessary porosity as well as improved extensibility leading to improved conformability, tactile manipulability, moldability, and palpability. Several important criteria for choosing a fabric which will provide the characteristics necessary for purposes of the present invention include: (1) lengthwise extensibility and conformability after mechanical compaction, and the related characteristics of moldability, tactility, and palpability once the fabric has been resin impregnated; (2) resin loading capacity; and (3) porosity. It is important that each of these parameters be carefully controlled in providing fabrics which will successfully form orthopedic casting materials within the scope of the present invention.

Extensibility is important from the standpoint that the fabric must be extensible enough along its length, i.e., in the elongated direction, so that the resultant orthopedic casting material can be made to substantially conform to the body pan to which it is applied. Materials which are not sufficiently extensible in the elongated direction do not conform well to the body pan when wrapped therearound, often resulting in undesirable wrinkles or folds in the material. On the other hand, the extensibility of the fabric in the elongated direction should not be so high that the material is too stretchy, resulting in a material structure which may be deformed to the extent that resin holding capacity and porosity are substantially reduced.

For purposes of the present invention, the fabric, after mechanical compaction, should have from about 10% to about 200% extensibility in the elongated direction when a 268 gram load or force is applied across a 1 cm section of the fabric, and preferably from about 25% to about 75% extensibility in the elongated direction when a 268 gram load or force is applied across a 1 cm section of the fabric, and more preferably from about 35% to about 65% extensibility in the elongated direction when a 268 gram load or force is applied across a 1 cm section of the fabric.

Although not nearly as critical, it is also desirable that the fabric employed have some extensibility along its width, i.e., in the direction transverse to the elongated direction. Thus although the fabric may have from 0% to 100% extensibility in the transverse direction, it is presently preferable to use a fabric having from about 1% to about 30% extensibility in the transverse direction when a 268 gram load or force is applied across a 1 cm section of the fabric. The mechanical compaction process previously described generally only imparts extensibility in the elongated direction. However, it is anticipated that one might mechanically compact a fabric twice, i.e., once in the elongated direction and a second time in the transverse direction, thereby imparting biaxial extensibility. Alternatively, both longitudinal and transverse compaction may be imparted simultaneously, e.g., both longitudinal and transverse compaction may be accomplished prior to the setting step.

The fabrics of the present invention, after mechanical compaction, although stretchable, are preferably not overly elastic or resilient. Fabrics which am overly elastic, when used as backings for orthopedic bandages, tend to cause undesirable constriction forces around the wrapped limb or body part. Thus, once the resin impregnated fabric has been stretched and applied around a body part, the stretched material preferably maintains its shape and does not resort back to its unstretched position.

The resin loading capacity or ability of the fabric to hold resin is important from the standpoint of providing an orthopedic casting material which has sufficient strength to efficaciously immobilize a body part. The surface structure of the fabric, including the fibers, interstices, and apertures, is very important in providing proper resin loading for purposes of the present invention. In this regard, the interstices between the fibers of each fiber bundle must provide sufficient volume or space to hold an adequate mount of resin within the fiber bundle to provide the strength necessary; while at the same time, the apertures between fiber bundles preferably remain sufficiently unoccluded such that adequate porosity is preserved once the resin is applied. Thus, the interstices between fibers are important in providing the necessary rosin loading capacity, while the apertures are important in providing the necessary porosity for the finished cast. However, a balancing of various parameters is needed to achieve both proper resin loading and porosity. The fabric should have preferably between about 6 and 70 openings (i.e., apertures) per square cm, more preferably between about 10 and 50 openings per square cm, and most preferably between about 20 and 40 openings per square cm.

As used herein, a "mechanically compacted" fiberglass sheet is one in which extensibility is imparted to the fabric due to overlapping of successive loops by the mechanical compaction processes described herein. The mechanical compaction process imparts extensibility to the fabric by mechanically compacting the loops of the knit while not further distorting fiber bundles. Typically, when a fabric is knitted the inside surfaces of two adjacent rows of loops are in contact or nearly in contact. This contact is the result of the fabric being under tension while the knit is being formed. Each successive row of loops (i.e., chain stitches) is, in effect, formed against the preceding row of loops. The mechanical compaction process of the instant invention imparts fabric compaction by overlapping adjacent rows of loops and setting or annealing the fabric in the compacted form. Extensibility is imparted to the fabric due to the overlap of the rows. When tension is again applied to the fabric the loops can return to their original "contacting" position, i.e., the position they occupied when originally knit. Preferably, the tape is further heat set to anneal the fibers in this state.

In one embodiment of the present invention, a fiberglass fabric knit according to the process described in U.S. Pat. No. 4,609,578, which is herein incorporated by reference, is laid on a smooth urethane belting material prior to being heat set. The fabric is then sprayed with water to cause the fabric to cling to the belting material, and compacted by hand to provide the desired compaction of the fabric compared to its uncompacted knit structure. The compacted fabric is then heated by hot air to "set" the starch sizing on the fibers. Alternatively, the fibers may be "tacked" together using any suitable glue or adhesive, e.g., a spray adhesive: The starch-setting (or glue) helps hold the compacted tape in a compacted form for subsequent processing. The compacted tape is then wound on a core and heat set as described in U.S. Pat. No. 4,609,578, and then coated with a liquid resin.

In an alternative embodiment of the present invention the compaction process may be performed by an automated process as described herein. A fiberglass fabric knit according to the process described in U.S. Pat. No. 4,609,578 is unwound from a roll into a warm water bath. The web is then passed over a nip roller and laid onto a moving apertured stainless steel belt. The moving belt carries the web toward a open cell polyurethane foam coated compactor roll, whose surface is traveling at a speed slower than the stainless steel belt, so as to cause compaction of the web. The compacted web is then carried by the belt past a vacuum manifold so as to remove any excess water and then past a heat source, such as an infrared oven, to set the starch sizing on the fibers. Alternatively, the fibers may be "rocked" together using any suitable glue or adhesive, e.g., a spray adhesive. This starch-setting helps hold the compacted tape in a compacted form for subsequent processing. Using the Starch binder already coated on commercially available fiberglass to set the tape is particularly preferred since no additional organic material is needed. This ensures that in the subsequent heat treatment process a low and controllable annealing temperature is maintained. The compacted tape is then wound on a core and heat set as described in U.S. Pat. No. 4,609,578, and then coated with a liquid resin. The foam coated roll may alternatively be coated with any suitable material which creates a differential coefficient of friction between: (1) the roll and the fabric; and (2) the belt and the fabric. Likewise, the moving belt need not be restricted to stainless steel. Any suitable belting material may be employed. Preferably, the belting material has sufficient apertures so that any excess water may be drained away therefrom.

Suitable fabrics, after mechanical compaction, arc compacted to between about 10 and 65 percent of their original dimension. More preferably, the fabric is compacted to between about 20 and 60 percent of its original dimension and most preferably, the fabric is compacted to between about 30 and 50 percent of its original dimension.

The curable resins useful in this invention arc resins which can be used to coat a sheet material and which can then be cured to reinforce the sheet material. The resin is curable to a crosslinked thermoset state. The preferred curable resins are fluids, i.e., compositions having viscosities between about 5 Pa s and about 500 Pa s, preferably about 10 Pa s to about 100 Pa s.

The resin used in the casting material of the invention is preferably any curable resin which will satisfy the functional requirements of an orthopedic east. Obviously, the resin must be nontoxic in the sense that it does not give off significant mounts of toxic vapors during curing which may be harmful to either the patient or the person applying the cast and also that it does not cause skin irritation either by chemical irritation or the generation of excessive heat during cure. Furthermore, the resin must be sufficiently reactive with the curing agent to insure rapid hardening of the cast once it is applied but not so reactive that it does not allow sufficient working time to apply and shape the cast. Initially, the casting material must be pliable and formable and should adhere to itself. Then in a short time following completion of cast application, it should become rigid or, at least, semi-rigid, and strong to support loads and stresses to which the cast is subjected by the activities of the wearer. Thus, the material must undergo a change of state from a fluid-like condition to a solid condition in a matter of minutes.

The preferred resins are those cured with water. Presently preferred are urethane resins cured by the reaction of a polyisocyanate and a polyol such as those disclosed in U.S. Pat. No. 4,131,114. A number of classes of water-curable resins known in the an arc suitable, including polyurethanes, cyanoacrylate esters, and, when combined with moisture sensitive catalysts, epoxy resins and prepolymers terminated at their ends with trialkoxy- or trihalo-silane groups. For example, U.S. Pat. No. 3,932,526 discloses that 1,1-bis(perfluoromethylsulfonyl)-2-aryl ethylenes cause epoxy resins containing traces of moisture to become polymerized.

Resin systems other that those which are water-curable may be used, although the use of water to activate the hardening of an orthopedic casting tape is most convenient, safe and familiar to orthopedic surgeons and medical casting personnel. Resin systems such as that disclosed in U.S. Pat. No. 3,908,644 in which a bandage is impregnated with difunctional acrylates or methacrylates, such as the bis-methacrylate ester derived from the condensation of glycidyl methacrylate and bisphenol A (4,4'-isopropylidenediphenol) are suitable. The resin is hardened upon wetting with solutions of a tertiary amine and an organic peroxide. Also, the water may contain a catalyst. For example, U.S. Pat. No. 3,630,194 proposes an orthopedic tape impregnated with acrylamide monomers whose polymerization is initiated by dipping the bandage in an aqueous solution of oxidizing and reducing agents (known in the an as a redox initiator system). The strength, rigidity and rate of hardening of such a bandage is subjected to the factors disclosed herein.

Some presently more preferred resins for use in the present invention are water-curable, isocyanate-functional prepolymers. Suitable systems of this type are disclosed, for example, in U.S. Pat. No. 4,411,262, and in U.S. Pat. No. 4,502,479. Preferred resin systems are disclosed in U.S. Pat. No. 4,667,661 and U.S. patent application Ser. No. 07/376,421. The following disclosure relates primarily to the preferred embodiment of the invention wherein water-curable isocyanate-functional prepolymers are employed as the curable resin. A water-curable isocyanate-functional prepolymer as used herein means a prepolymer derived from polyisocyanate, preferably aromatic, and a reactive hydrogen compound or oligomer. The prepolymer has sufficient isocyanate-functionality to cure upon exposure to water, e.g., moisture vapor, or preferably liquid water.

It is preferred to coat the resin onto the fabric as a polyisocyanate prepolymer formed by the reaction of an isocyanate and a polyol. It is preferred to use an isocyanate which has low volatility such as diphenylmethane diisocyanate (MDI) rather than a more volatile material such as toluene diisocyanate (TDI). Suitable isocyanates include 2,4-toluene diisocyanate, 2,6-toluene diisocyanate, mixture of these isomers, 4,4'-diphenylmethane diisocyanate, 2,4'-diphenylmethane diisocyanate, mixture of these isomers together with possible small quantifies of 2,2'-diphenylmethane diisocyanate (typical of commercially available diphenylmethane diisocyanate), and aromatic polyisocyanates and their mixture such as are derived from phosgenation of the condensation product of aniline and formaldehyde. Typical polyols for use in the prepolymer system include polypropylene ether glycols (available from Arco Chemical Co. under the trade name Arcol TM PPG and from BASF Wyandotte under the trade name Pluracol TM ), polytetramethylene ether glycols (Polymeg TM from the Quaker Oats Co.), polycaprolactone diols (Niax TM PCP series of polyols from Union Carbide), and polyester polyols (hydroxyl terminated polyesters obtained from esterification of dicarboxylic acids and diols such as the Rucoflex TM polyols available from Ruco division, Hooker Chemical Co.). By using high molecular weight polyols, the rigidity of the cured resin can be reduced.

An example of a resin useful in the casting material of the invention uses an isocyanate known as Isonate TM 2143L available from the Upjohn Company (a mixture containing about 73% of MDI) and a polypropylene oxide polyol from. Union Carbide known as Niax TM PPG725. To prolong the shelf life of the material, it is preferred to include from 0.01 to 1.0 percent by weight of benzoyl chloride or another suitable stabilizer.

The reactivity of the resin once it is exposed to the water curing agent can be controlled by the use of a proper catalyst. The reactivity must not be so great that: (1) a hard film quickly forms on the resin surface preventing further penetration of the water into the bulk of the resin; or (2) the cast becomes rigid before the application and shaping is complete. Good results have been achieved using 4-[2-[1-methyl-2-(4-morpholinyl)ethoxy]ethyl]morpholine (MEMPE) prepared as described in U.S. Pat. No. 4,705,840, the disclosure of which is incorporated by reference, at a concentration of about 0.05 to about 5 percent by weight.

Foaming of the resin should be minimized since it reduces the porosity of the cast and its overall strength. Foaming occurs because carbon dioxide is released when water reacts with isocyanate groups. One way to minimize foaming is to reduce the concentration of isocyanate groups in the prepolymer. However, to have reactivity, workability, and ultimate strength, an adequate concentration of isocyanate groups is necessary. Although foaming is less at low resin contents, adequate resin content is required for desirable cast characteristics such as strength and resistance to peeling. The most satisfactory method of minimizing foaming is to add a foam suppressor such as silicone Antifoam A (Dow Corning), or Antifoam 1400 silicone fluid (Dow Corning) to the resin. It is especially preferred to use a silicone liquid such as Dow Corning Antifoam 1400 at a concentration of about 0.05 to 1.0 percent by weight. Water-curable resins containing a stable dispersion of hydrophobic polymeric particles, such as disclosed in U.S. patent application Ser. No. 07/376,421 and laid open as European Published Patent Application EPO 0 407 056, may also be used to reduce foaming.

Also included as presently more preferred resins in the instant invention are non-isocyanate resins such as water reactive liquid organometallic compounds. These resins are especially preferred as an alternative to isocyanate resin systems. Water-curable resin compositions suitable for use in an orthopedic cast consist of a water-reactive liquid organometallic compound and an organic polymer. The organometallic compound is a compound of the formula $(R^1O)_xMR^2_{(y-x)}$ wherein: each $R^1$ is independently a $C_1$–$C_{100}$ hydrocarbon group, optionally interrupted in the backbone by 1–50 nonperoxide —O—, —S—, —C(O)—, or —N— groups; each $R^2$ is independently selected from the group consisting of hydrogen and a $C_1$–$C_{100}$ hydrocarbon group, optionally interrupted in the backbone by 1–50 nonperoxide —O—, —S—, —C(O)—, or —N— groups; x is an integer between 1 and y, inclusive; y is the valence of M; and M is boron, aluminum, silicon, or titanium. The organic polymer is either an addition polymer or a condensation polymer. Addition polymers are preferably utilized as the organic polymer constituent. Particularly useful addition polymers are those made from ethylenically unsaturated monomers. Commercially available monomers, from which such addition polymers can be formed, include but are not limited to, ethylene; isobutylene, 1-hexene, chlorotrifluoroethylene, vinylidene chloride, butadiene, isoprene, styrene, vinyl napthalene, ethyl acrylate, 2-ethylhexyl acrylate, tetrahydrofurfuryl acrylate, benzyl acrylate, poly(ethylene oxide) monoacrylate, heptafluorobutyl acrylate, acrylic acid, methyl methacrylate, 2-dimethylaminoethyl methacrylate, 3-methacryloxypropyltris(trimethylsiloxy) silane, isobutyl methacrylate, itaconic acid, vinyl acetate, vinyl stearate, N,N-dimethylacrylamide, tert-butyl acrylamide, acrylonitrile, isobutyl vinyl ether, vinyl pyrolidinone, vinyl azlactone, glycidyl methacrylate, 2-isocyanatoethyl methacrylate, maleic anhydride, vinyl triethoxysilane, vinyl tris(2-methoxyethoxy)silane, and 3-(trimethoxysilyl)propyl methacrylate. Polymers bearing hydrolyzable functionality are preferred. An acidic or basic catalyst may be used to accelerate the water cure of these compositions. Strong acid catalysts are preferred.

Optionally, the scrims of the present invention are coated with a resin which incorporates microfiber fillers. These preferred orthopedic bandages enjoy many benefits, for example, resins which incorporate microfiber fillers exhibit: a dramatic increase in strength when coated on the backings of the present invention; an increased "early strength" upon curing; an improved durability and increased modulus; better layer-to-layer lamination strength; a lower exotherm upon setting; and a lower effective resin cost compared to resins which do not incorporate such microfiber fillers. In addition, resin suspensions employing the microfiber filers of the present invention exhibit generally very little increase in resin viscosity—thereby ensuring easy unwind of the casting bandage and good handling properties such as drapability.

The microfiber fillers useful in this invention are generally characterized as being short fibers having an aspect ratio greater than five to one. "Aspect ratio" as used herein, refers to the ratio of the fiber's length to its diameter. For fibers having an irregular or non-circular cross section, the "diameter" of the microfiber shall be equal to the largest width across the microfiber. Blends of microfibers having different aspect ratios may be utilized in the casting tapes of the present invention. For purposes of this invention, when blends of microfibers are employed, the aspect ratio of the blend of microfibers refers to the mean aspect ratio. Preferred microfiber fillers or blends have an aspect ratio between 5:1 and 200:1. More preferably, the aspect ratio of the microfiber is between 5:1 and 50:1. Most preferably, the aspect ratio of the microfiber is between 10:1 and 30:1.

Suitable microfibers have a mean diameter between approximately 1 and 60 microns ($\mu$m) and a mean length between approximately 25 and 1000 $\mu$m. Preferred microfiber fillers or blends have a mean diameter between 0.1 and 60 $\mu$m, more preferably, the mean diameter of the microfiber is between 1 and 40 $\mu$m, and most preferably, the mean diameter of the microfiber is between 1 and 30 $\mu$m. Preferred microfiber fillers or blends have a mean length between 25 and 5,000 $\mu$m, more preferably, the mean length of the microfiber is between 30 and 1,000 $\mu$m, and most preferably, the mean length of the microfiber is between 30 and 500 $\mu$m. The presently most preferred filler, Nyad G Wollastokup, is characterized primarily by mesh size. Ninety percent of this material passes through a 200 mesh screen (127$\times$127 $\mu$m hole size). Visual observation of scanning electron microscope "SEM" photos indicates the average fiber diameter to be in the range of 10 to 30 $\mu$m and the average fiber length to be in the range of 200 to 400 $\mu$m.

The microfiber can be naturally occurring inorganic fibers, synthetic inorganic fibers, naturally occurring organic fibers, and synthetic organic fibers. The fiber, if inorganic, can be amorphous, single crystal (e.g., a whisker), polycrystalline, or multiphase. Blends of fibers can be employed if desired.

The various structural features of inorganic fibers reflect the complex interaction of fiber chemistry and fiber formation technique. Amorphous inorganic fibers such as fiberglass and fused silica fibers are manufactured by melt spinning. Although these fibers possess relatively high tensile strength, their modulus is among the lowest of inorganic fibers. On the other hand, single crystal fibers, sometimes referred to by those skilled in the art as "whiskers," are generally chemically pure and highly ordered. This results in strength approaching the theoretical limit, making them the strongest of all fibers.

Whiskers are the ultimate-strength short-fiber material. They are small (being submicron to several microns in diameter), single-crystal fibers with a high degree of crystalline perfection. In general, the smaller the whisker, the greater the perfection. This perfection results from low dislocation density, low void content, low internal and surface imperfections, and no grain boundaries.. Whiskers typically have high mechanical properties: for example, a tensile strength between 13 GPa to 32 GPa (10 times that of most conventional fibers), a modulus of 450 GPa to 900 GPa, an elongation of 3 to 4 percent, and an exceptionally high degree of toughness and nonfriability.

Microfibers can be made relatively quickly by low-cost processing techniques, such as precipitation from a supersaturated solution. However, because they are made rapidly and from a liquid they do not possess the purity and crystalline perfection of a true whisker. These fibers are generally polycrystalline fiber bundles with grain boundaries and they often contain voids, dislocations, and crystalline imperfections rarely found in a true whisker. Nevertheless, such microfibers have, in general, much superior properties than the cured matrix resin which surrounds them and are suitable for use in the casting materials of the present invention.

Suitable inorganic microfibers are presently preferred and include, for example, ceramic fibers formed of pure or mixed metal oxides, boron fibers, milled fiberglass, potassium titanate fibers, calcium sulfate fibers (e.g., Franklin Fiber), and processed mineral fibers such as asbestos (i.e., chrysotile or hydrated magnesium silicate), and wollastonite (i.e., calcium metasilicate—$CaSiO_3$). Asbestos, while suitable, is not preferred at the present time because of health considerations. Suitable organic. microfibers include, for example, carbon/graphite fibers and aramid fibers.

Franklin Fiber filler is a whisker form of calcium sulfate which differs significantly from typical calcium sulfate fillers. Franklin Fiber filler is made from gypsum using a hydrothermal synthesis. During this process, gypsum is converted to single crystal, microfibers of calcium sulfate hemihydrate. Subsequent dead burning produces the anhydrous form. Notably, for water reactive resin systems, only the anhydrous form of the microfiber filler is suitable as the water of the hemihydrate form, although "bound" and pan of the crystal structure, will cause the resin to react prematurely.

Suitable microfiber fillers of the present invention are incorporated into the liquid resin in an amount sufficient to provide the desired increased strength while not adversely affecting the uncured resin suspension viscosity. A suitable amount of a filler in a resin will result in a suspension having a viscosity prior to being cured of less than 500 Pa s as measured at 23° C. using a Brookfield RTV Rotovisco viscometer with either a #6 or #7 spindle (viscosities greater than 100 Pa s should be measured with the #7 spindle). Preferred suspensions have a viscosity prior to being cured of between about 5 and 100 Pa s, more preferably between about 10 and 70 Pa s and most preferably between about 30 and 70 Pa s. While the exact mount of microfiber filler can not be precisely determined owing to factors such as initial resin viscosity, microfiber type, microfiber size and aspect ratio, suitable suspensions for use in the present invention contain up to about 40 percent microfiber filler. Preferred suspensions of resin and microfiber filler contain between about 3 and 35 percent microfiber filler. More preferred suspensions of resin and microfiber filer contain between about 7 and 25 percent microfiber filler. Most preferred suspensions of resin and microfiber filler contain between about 10 and 25 percent microfiber filler.

If desired, the microfiber fillers may be surface treated using silanes, titanates, zirconates and the like to enhance resin bonding, ease of mixing, and compatibility. The surface treatment may be performed prior to incorporation of the microfiber into the resin or in-situ, i.e., the surface treatment agent may be incorporated into the suspension for later reaction with the filler.

The following examples are offered to aid in understanding of the present invention and are not to be construed as limiting the scope thereof. Unless otherwise indicated, all pans and percentages are by weight.

EXAMPLES

Example 1

Mechanical Compaction of a Fiberglass Knit Casting Tape

A fiberglass fabric knit according to the process described in U.S. Pat. No. 4,609,578, which is herein incorporated by reference, was laid on a smooth urethane belting material prior to being heat sat. Two marks, 40.6 cm apart, were made on the tape. The fabric was then sprayed with water to cause the fabric to cling to the belting material, and compacted by hand to fit the 40.6 cm marks between two marks set 34.3 cm apart on the belt. This effectively provides 18 percent compaction of the fabric compared to its uncompacted knit structure. This process was repeated until the desired length of fabric was compacted. The compacted fabric was then heated by hot air to "set" the starch sizing on the fibers. This starch-setting helps hold the compacted tape in a compacted form for subsequent processing. The tape was then wound on a core and heat set as described in U.S. Pat. No. 4,609,578. The resulting fabric was then coated with a liquid isocyanate-terminated polyurethane prepolymer as described in U.S. Pat. No. 4,609,578 to yield a casting tape having 40.4 percent by weight resin. After resin coating the casting tape had 41.8 percent stretch when a 0.292N/mm force per unit width was applied.

Ring strength was measured as described in the following procedure. A cylindrical ring comprising 6 layers of the resin-coated material was formed by taking a roll of the resin-coated material from its storage pouch and immersing the roll completely in deionized water having a temperature of about 27° C. for about 30 seconds. The width of the ring formed was the same as the width of the resin-coated material employed, namely, 7.62 cm. The roll of resin-coated material was then removed from the water and the material was wrapped around a 5.08 cm diameter mandrel covered with a thin stockinet (such as 3M Synthetic Stockinet MSO2) to form 6 complete uniform layers using a controlled wrapping tension of about 45 grams per centimeter width of material. Each cylinder was completely wound within 30 seconds after its removal from the water.

After 7 to 20 minutes from the initial immersion in water, the cured cylinder was removed from the mandrel, and after 7.5 or 30 minutes from the initial immersion in water its strength was determined. Ring strength was also determined 24 hours after initial immersion in water, i.e., those samples were allowed to cure for 24 hours in a controlled atmosphere of 25° C.±2° C. and 55%±5% relative humidity prior to testing.

At the appropriate time each cylinder was then placed in a fixture in a commercial testing machine, e.g., an Instron instrument, and compression loads were applied to the cylindrical ring sample along its exterior and parallel to its axis. The cylindrical ring was placed lengthwise between the two bottom bars of the fixture (the bars being 1.9 cm wide, 1.3 cm in height, and 15.2 cm long), with the bars spaced about 4 cm apart. The inside edges of the bars were machined to form a curved surface having a 0.31 cm radius. A third bar (0.63 cm wide, 2.5 cm high, and 15.2 cm long) was then centered over the top of the cylinder, also parallel to its axis. The bottom or contacting edge of the third bar was machined to form a curved surface having a 0.31 cm radius. The third bar was brought down to bear against and crush the cylinder at a speed of about 5 cm/min. The maximum peak force which was applied while crushing the cylinder was then recorded as the "ring strength," which in this particular instance is the "dry strength" (expressed in terms of force per unit length of the cylinder, i.e., newtons/cm). For each material, at least 5 samples were tested, and the average peak force applied was then calculated and reported as the dry "ring strength." The results of ring strength testing is listed in Table 1a.

TABLE 1a

| Test | Result (N/cm) |
|---|---|
| 7.5 minute dry ring strength | 8.95 |
| 30 minute dry ring strength | 28.2 |
| 24 hour dry ring strength | 89.4 |

Example 2

Mechanical Compaction of a Fiberglass Knit Casting Tape

A fiberglass fabric knit according to the material and process described in U.S. Pat. No. 4,609,578, which is herein incorporated by reference, was unwound from a roll into a warm water bath. The web was then passed over a nip roller and laid onto a moving apertured stainless steel belt. The moving belt carried the web toward a foam coated compactor roll, whose surface was traveling at a speed slower than the stainless steel belt, so as to cause compaction of the web. The compacted web was then carried by the belt past a vacuum manifold so as to remove any excess water and then past a heat source, such as an infrared oven, to set the tape. This starch-setting helps hold the compacted tape in a compacted form for subsequent processing. The compacted tape was then wound on a core and heat set as described in U.S. Pat. No. 4,609,578. The resulting fabric was then coated with a liquid isocyanate-terminated polyurethane prepolymer as described in U.S. Pat. No. 4,609,578 to yield a casting tape having approximately 40 percent by weight resin. After resin coating the casting tape had greater extensibility than a tape which was not mechanically compacted.

Various modifications and alterations of this invention will be apparent to those skilled in the art without departing from the scope and spirit of this invention, and it should be understood that this invention is not limited to the illustrative embodiments set forth herein.

What is claimed is:

1. An article, comprising:
   a mechanically compacted fiberglass fabric sheet, wherein said fabric comprises adjacent rows of overlapping loops, said loops being mechanically compacted to a non-contacting position and said fabric sheet then being heat set; and
   a curable liquid resin coated onto said fabric sheet.

2. An article, as defined in claim 1, further comprising:
   a microfiber filler associated with said resin, wherein said microfiber filler has an aspect ratio between about 5:1 and 200:1.

3. An article, as defined in claim 1, wherein said sheet has from about 25% to about 75% extensibility in the elongated direction when a 268 gram load or force is applied across a 1 cm section of the fabric.

4. An article, as defined in claim 2, wherein said sheet has from about 35% to about 65% extensibility in the elongated direction when a 268 gram load or force is applied across a 1 cm section of the fabric.

5. An article, as defined in claim 3, wherein said curable resin is a water-curable resin comprising isocyanate-functional prepolymers.

6. An article, as defined in claim 3, wherein said curable resin is a water-curable resin comprising a water-reactive liquid organometallic compound and an organic polymer.

7. An article, as defined in claim 4, wherein said fabric has between about 6 and 70 openings per square cm.

8. An article, as defined in claim 1, wherein said fabric was compacted to between about 10 and 65 percent of its original dimension.

9. An article, as defined in claim 1, wherein said fabric was compacted to between about 20 and 50 percent of its original dimension.

10. An article, according to claim 9, wherein said resin has a viscosity between about 10 Pa s and 100 Pa s.

11. An article, as defined in claim 1, wherein said article is selected from the group consisting of orthopedic casts, orthopedic splints, braces, supports, protective shields, and orthotics.

12. An article, as defined in claim 1, wherein said article is in the form of an orthopedic casting bandage.

13. An orthopedic casting bandage, as defined in claim 12, wherein said fiberglass sheet further comprises a starch sizing.

14. An orthopedic casting bandage, as defined in claim 12, wherein said casting bandage further comprises: between 3 and 35 percent of a microfiber filler associated with said resin, wherein said microfiber filler has an aspect ratio between about 5:1 and 200:1.

15. An orthopedic casting bandage, as defined in claim 12, wherein said fabric has between about 6 and 70 openings per square cm.

16. An orthopedic casting bandage, as defined in claim 12, wherein said fabric was compacted to between about 10 and 65 percent of its original dimension.

17. An orthopedic casting bandage, as defined in claim 12, wherein said fabric was compacted to between about 20 and 50 percent of its original dimension.

18. An orthopedic casting bandage, as defined in claim 12, wherein said sheet has from about 35% to about 65% extensibility in the elongated direction when a 268 gram load or force is applied across a 1 cm section of the fabric.

19. An orthopedic casting bandage, as defined in claim 12, wherein said resin has a viscosity between about 10 Pa s and 100 Pa s.

* * * * *

UNITED STATES PATENT AND TRADEMARK OFFICE
CERTIFICATE OF CORRECTION

PATENT NO.: 5,449,550

DATED: September 12, 1995

INVENTOR(S): Rafael M. Yasis, Scott A. Neamy and Matthew T. Scholz

It is certified that error appears in the above-identified patent and that said Letters Patent is hereby corrected as shown below:

In the Abstract, line 3, "item" should read -- resin --.

Col. 1, line 5, "08/008/161" should read -- 08/008,161 --.

Col. 1, line 57, "cam" should read -- care --.

Col. 2, line 1, "da" should read -- do --.

Col. 3, line 15, "Pt." should read -- Pat. --.

Col. 3, line 56, "rosin" should read -- resin --.

Col. 4, line 18, "pan" should read -- part --.

Col. 4, line 20, "pan" should read -- part --.

Col. 4, line 59, "am" should read -- are --.

Col. 5, line 14, "rosin" should read -- resin --.

UNITED STATES PATENT AND TRADEMARK OFFICE
CERTIFICATE OF CORRECTION

PATENT NO.: 5,449,550

DATED: September 12, 1995

INVENTOR(S): Rafael M. Yasis, Scott A. Neamy and Matthew T. Scholz

It is certified that error appears in the above-identified patent and that said Letters Patent is hereby corrected as shown below:

Col. 5, line 56, delete the colon and insert a period after "adhesive".

Col. 6, line 8, "rocked" should read -- tacked --.

Col. 6, line 28, "arc" should read -- are --.

Col. 6, line 35, "arc" should read -- are --.

Col. 6, line 44, "east" should read -- cast --.

Col. 6, line 67, "an arc" should read -- art are --.

Col. 7, line 24, "an" should read -- art --.

Col. 9, line 12, "pyrolidinone" should read -- pyrrolidinone --.

Col. 9, line 32, "filers" should read fillers --.

Col. 11, line 22, "filer" should read -- filler --.

UNITED STATES PATENT AND TRADEMARK OFFICE
CERTIFICATE OF CORRECTION

PATENT NO.: 5,449,550

DATED: September 12, 1995

INVENTOR(S): Rafael M. Yasis, Scott A. Neamy and Matthew T. Scholz

It is certified that error appears in the above-identified patent and that said Letters Patent is hereby corrected as shown below:

Col. 11, line 35, "pans" should read -- parts --.

Col. 11, line 45, "sat" should read -- set --.

Signed and Sealed this

Fourth Day of February, 1997

Attest:

BRUCE LEHMAN

Attesting Officer

Commissioner of Patents and Trademarks